United States Patent [19]

Meyer et al.

[11] B 4,001,259

[45] Jan. 4, 1977

[54] 3,6-DIAMINO-3,4-DIHYDRO-2-PYRIDONES

[75] Inventors: Horst Meyer; Friedrich Bossert, both of Wuppertal; Wulf Vater, Opladen; Kurt Stoepel, Wuppertal, all of Germany

[73] Assignee: Bayer Aktiengesellschaft, Germany

[22] Filed: Jan. 30, 1975

[21] Appl. No.: 545,299

[44] Published under the second Trial Voluntary Protest Program on February 24, 1976 as document No. B 545,299.

[30] Foreign Application Priority Data

Feb. 9, 1974 Germany ............... 2406200

[52] U.S. Cl. ............... 260/295.5 A; 260/256.4 R; 260/287 R; 260/294.8 D; 260/294.8 F; 260/294.8 G; 260/295.5 R; 260/294.9; 260/295.5 B; 424/251; 424/258; 424/266

[51] Int. Cl. .......................... C07d 213/56

[58] Field of Search ............ 260/294.8 F, 294.8 G, 260/295.5 A, 294.9; 424/266

[56] References Cited

UNITED STATES PATENTS 3,860,601 1/1975 Meyer et al. ............... 260/295.5 R
3,862,161 1/1975 Bossert et al. ............... 260/295.5 R

*Primary Examiner*—Alan L. Rotman

[57] ABSTRACT

3,6-Diamino-3,4-dihydro-2-pyridones of the formula

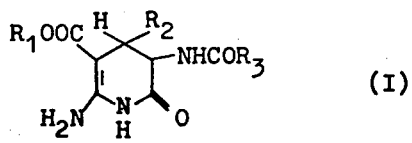

(I)

wherein $R_1$ is straight or branched chain alkyl or alkenyl or said alkyl or alkenyl interrupted by 1 or 2 oxygen atoms;

$R_2$ is straight or branched chain alkyl; alkenyl; alkynyl; cycloalkyl; cycloalkenyl; cycloalkynyl; aryl unsubstituted or substituted by 1 to 3 of the same or different substituents selected from the group consisting of alkyl, alkoxy, halogen, nitro, cyano, trifluoromethyl, carbalkoxy and $SO_n$-alkyl wherein $n$ is 0 to 2; naphthyl; quinolyl; isoquinolyl; pyridyl, pyrimidyl, thienyl; or furyl; and $R_3$ is straight or branched chain alkyl; or aryl unsubstituted or substituted by alkyl, alkoxy, nitro, trifluoromethyl or halo;

are produced by reacting a 4-ylidene-1, 3-oxazolin 5-one of the formula

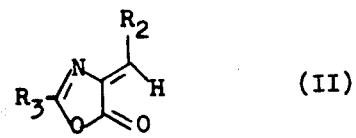

(II)

wherein $R_2$ and $R_3$ are as above defined, with an amidinoacetic acid ester of the formula

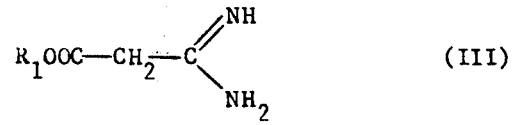

(III)

or a salt thereof, wherein $R_1$ is as above defined, in the presence of an inert inorganic solvent and either in the presence of or in the absence of a catalytic amount of an alkali alcohol at a temperature of from about 20° C to about 200° C.

10 Claims, No Drawings

3,6-DIAMINO-3,4-DIHYDRO-2-PYRIDONES

The present invention is concerned with 3,6-diamino-3,4-dihydro-2-pyridones, to a process for their production, to pharmaceutical compositions utilizing said compounds as the active agent, and to methods of treatment utilizing said compounds as the active agent, particularly for the purpose of effecting coronary vessel dilation in humans and animals and treating hypertension in humans and animals.

It is known in the art that the reaction of benzylidenemalonic acid diethyl ester with 3-aminocrotonic acid ethyl ester gives a 3,4-dihydropyridone:

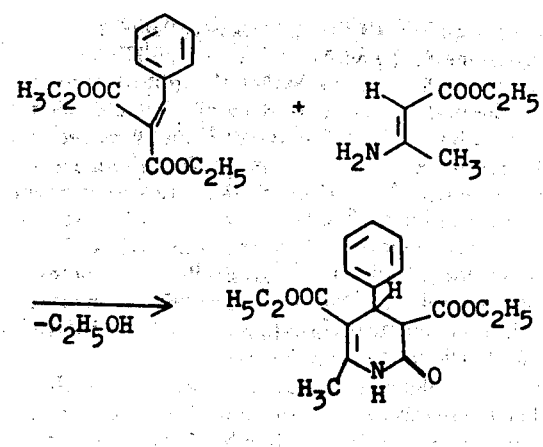

(See Knoevenagel and Fries, Ber. 31, 761 (1898)).

More particularly, the present invention is concerned with 3,6-diamino-3,4-dihydro-2-pyridones of the formula

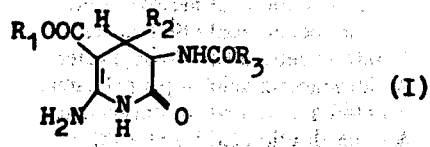

wherein
$R_1$ is straight or branched chain alkyl, especially lower alkyl; straight or branched chain alkenyl, especially lower alkenyl; straight or branched chain alkyl, especially lower alkyl, interrupted by 1 or 2 oxygen atoms; or straight or branched chain alkenyl, especially lower alkenyl, interrupted by 1 or 2 oxygen atoms;

$R_2$ is a saturated, partially unsaturated or unsaturated, straight, branched or cyclic hydrocarbon, especially a lower hydrocarbon such as lower alkyl, lower alkenyl, lower alkynyl, cycloalkyl of 3 to 7 carbon atoms, cycloalkenyl of 3 to 7 carbon atoms and cycloalkynyl of 3 to 3 carbon atoms; aryl, particularly aryl of 6 to 10 carbon atoms, unsubstituted or substituted by 1 to 3 of the same or different substituents selected from the group consisting of alkyl, especially lower alkyl, alkoxy, especially lower alkoxy, halo, nitro, cyano, trifluoromethyl, carbalkoxy, especially carb(lower alkoxy) and $SO_n$-alkyl, especially lower alkyl, wherein $n$ is 0, 1 or 2; naphthyl; quinolyl; isoquinolyl; pyridyl; pyrimidyl; thienyl; or furyl; and $R_3$ is straight or branched chain alkyl, especially lower alkyl, or aryl, especially phenyl, unsubstituted or substituted by alkyl, especially of 1 to 4 carbon atoms, alkoxy, especially of 1 to 4 carbon atoms, nitro, trifluoromethyl or halo.

The compounds of the present invention can be prepared by reacting a 4-ylidene-1,3-oxazolin-5-one of the formula

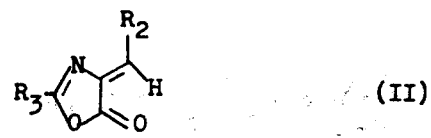

wherein $R_2$ and $R_3$ are as above defined, with an amidinoacetic acid ester of the formula

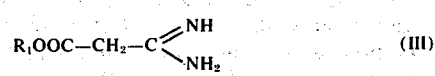

or a pharmaceutically acceptable, nontoxic salt thereof, wherein $R_1$ is as above defined, in the presence of an inert organic solvent and either in the presence or in the absence of catalytic amounts of an alkali alcohol, at a temperature of from about 20° C to about 200° C.

It is distinctly surprising that the reaction according to the present invention produces the new 3,6-diamino-3,4-dihydro-2-pyridones of the formula (I) in such good yields and such high purity, since, from the state of the art, an addition of the amidine group to the $\alpha,\beta$-unsaturated carbonyl group to give the dihydropyrimidones (IV) in accordance with the following equation would have had to have been expected:

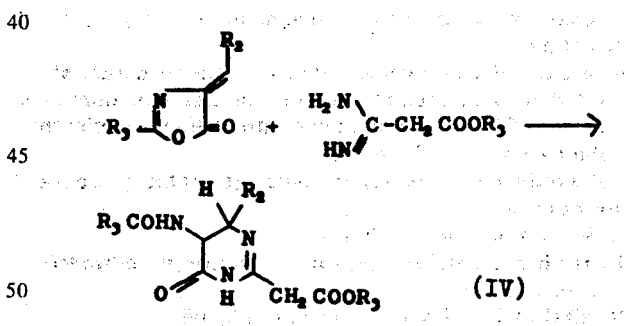

(compare E.F. Silversmith, J. Org. Chem. 27, 4090 (1962)).

However, this expected formation of compounds of the structure (IV) is not observed when carrying out the process according to the present invention.

An important advantage of the process according to the present invention is that it gives high yields and products of high purity and can be carried out as a one-step process with little technical effort and highly economically.

If 2-phenyl-4-(3'-nitrobenzylidene)-1,3-oxazolinone-5 and amidinoacetic acid ethyl ester are used as the starting components, the course of the reaction is represented by the following equation:

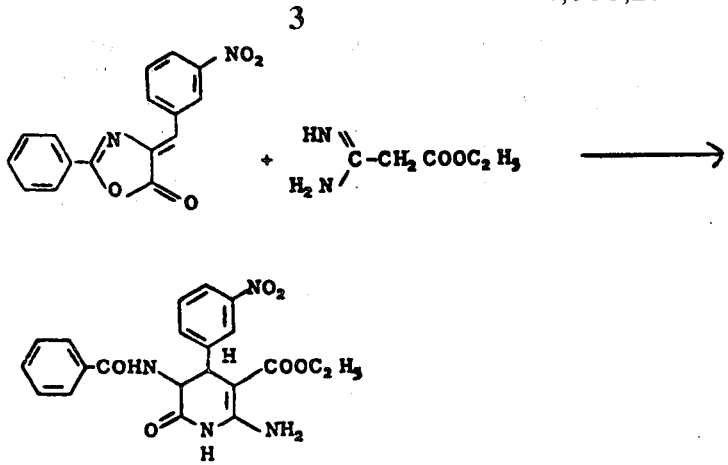

According to one embodiment of the present invention $R_1$ is straight or branched chain alkyl of 1 to 6 carbon atoms; straight or branched chain alkenyl of 2 to 6 carbon atoms; straight or branched chain alkyl of 1 to 6 carbon atoms interrupted by 1 oxygen atom; or straight or branched chain alkenyl of 2 to 6 carbon atoms interrupted by 1 oxygen atom;

$R_2$ is straight or branched chain alkyl of 1 to 6 carbon atoms; cycloalkyl of 3 to 6 carbon atoms; phenyl substituted by 1 or 2 of the same or different substitutents selected from the group consisting of alkyl of 1 to 4 carbon atoms, alkoxy of 1 to 4 carbon atoms, halo, nitro, cyano, trifluoromethyl, carb(lower alkoxy) of 1 to 4 carbon atoms in the alkyl moiety, and $SO_n$-alkyl of 1 to 4 carbon atoms wherein $n$ is 0 or 2; naphthyl; quinolyl; pyridyl; thenyl; or furyl; and $R_3$ is straight or branched chain alkyl of 1 to 4 carbon atoms; or phenyl unsubstituted or subsituted by alkyl of 1 or 2 carbon atoms, alkoxy of 1 or 2 carbon atoms, nitro, trifluoromethyl, fluoro, chloro or bromo.

According to another embodiment of the present invention $R_3$ is alkyl of 1 or 2 carbon atoms; or phenyl unsubstituted or substituted by alkyl of 1 or 2 carbon atoms, alkoxy of 1 or 2 carbon atoms, nitro, trifluoromethyl, fluoro, chloro or bromo.

According to another embodiment of the present invention $R_1$ is alkyl of 1 or 2 carbon atoms;

$R_2$ is phenyl unsubstituted or substituted by nitro or halo; and $R_3$ alkyl of 1 or 2 carbon atoms or phenyl.

According to another embodiment of the present invention $R_1$ is ethyl;

$R_2$ is phenyl; chlorophenyl; or nitrophenyl; and, $R_3$ is methyl or phenyl.

The 4-ylidene-1,3-oxazolin-5-ones of the formula (II) are either per se known or can be prepared according to techniques per se known. (See Org. Reactions, Vol. XV.)

The following 4-ylidene-1,3-oxazolin-5-ones are representative of those which can be used according to the present invention:

2-Phenyl-4-benzylidene-1,3-oxazolinone-5, 2-methyl-4-benzylidene-1,3-oxazolinone-5, 2-phenyl-4-(3'-nitrobenzylidene)-1,3-oxazolinone-5, 2-(4'-chlorophenyl)-4-(4''-chlorobenzylidene)-1,3-oxazolinone-5, 2-(4'-methoxyphenyl)-4-ethylidene-1,3-oxazolinone-5, 2-methyl-4-(2'-trifluoromethylbenzylidene)-1,3-oxazolinone-5, 2-phenyl-4-(2'-cyanobenzylidene)-1,3-oxazolinone-5, 2-methyl-4-(2'-naphthylidene)-1,3-oxazolinone-5, 2-methyl-4-(α-pyridylmethylidene)-1,3-oxazolinone-5, 2-ethyl-4-(2'-nitrobenzylidene)-1,3-oxazolinone-5, 2-isopropyl-4-benzylidene-1,3-oxazolinone-5, 2-(4'-methylphenyl)-4-benzylidene-1,3-oxazolinone-5, 2-methyl-4-(4'-methylbenzylidene-1,3-oxazolinone-5, 2-(4'-chlorophenyl)-4-(3'',4''-dichlorobenzylidene)-1,3-oxazolinone-5, 2-methyl-4-(2'-fluorobenzylidene)-1,3-oxazolinone-5, 2-methyl-4-(2'-thenylidene)-1,3-oxazolinone and 2-ethyl-4-(2'-furfurylidene)-1,3-oxazolinone-5.

The amidinoacetic acid esters of the formula (III) are either per se known or can be prepared according to techniques per se known. (See S. M. McElvain and B. E. Tate, J.A.C.S., 73, 2760 (1951).)

The following amidinoacetic acid esters are representative of those which can be used according to the present invention:

Amidinoacetic acid methyl ester,
Amidinoacetic acid ethyl ester,
Amidinoacetic acid n-propyl ester,
Amidinoacetic acid isopropyl ester,
Amidinoacetic acid propargyl ester,
Amidinoacetic acid butyl ester,
Amidinoacetic acid β-methoxy-ethyl ester
Amidinoacetic acid α-ethoxyethyl ester,
Amidinoacetic acid β-ethoxyethyl ester.

The amidines can either be used in the form of the free ester or in the form of a salt, preferably a pharmaceutically acceptable nontoxic salt such as the hydrohalides. The free ester may be liberated from the salt by means of basic agents such as alkali metal alcoholates.

All inert organic solvents may be used in the process of the present invention. These include alcohols such as methanol, ethanol and propanol; ethers such as dioxane and diethyl ether; glacial acetic acid; pyridine; dimethylformamide; dimethylsulphoxide; and acetonitrile.

While the reaction temperature can be varied within a substantial range as indicated above by the range of 20° to 200° C, according to a preferred embodiment the process of the present invention is carried out at the boiling point of the solvent.

The reaction can be carried out either at atmospheric pressure or at elevated pressure. Generally it is carried out at atmospheric pressure.

In carrying out the process of the present invention, the reactants are preferably employed in molar amounts.

The compounds of the present invention have a broad and diverse pharmacological spectrum of activity. In particular, the following types of activity have been demonstrated in animal experiments:

1. On parenteral, oral and perlingual administration the compounds produce a distinct and long-lasting dilation of the coronary vessels. This action on the coronary vessels is intensified by a simultaneous nitrite-like effect of reducing the load on the heart. They influence or modify the heart metabolism in the sense of an energy saving.
2. The compounds lower the blood pressure of normotonic and hypertonic animals and can thus be used as anti-hypertensive agents.
3. The excitability of the stimulus formation and excitation conduction system within the heart is lowered, so that an anti-fibrillation action demonstrable at therapeutic doses results.
4. The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system).
5. The compounds have strongly muscular-spasmolytic actions which manifest themselves on the smooth muscle of the stomach, the intestinal tract, the urogenital tract and the respiratory system.
6. The compounds influence the cholesterol level and lipid level of the blood.

The pharmaceutical compositions of the present invention contain a major or minor amount, preferably 0.5 to 90% by weight of active ingredient as above defined in combination with a pharmaceutically acceptable, nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 0.5 to 100 mg per kg of body weight per day. In some instances a sufficient therapeutic effect can be obtained at a lower dose, while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonat or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as a syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The medicaments can also be combined with free-flowing, inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coating to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low-melting, water soluble or insoluble solids such as polyethylene glycol, cocoa butter, higher esters as for example myristyl palmitate, or mixtures thereof.

Topical administration can be effected utilizing solid dosage unit forms such as powders or liquid or semi-liquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

While the routes of administration include oral, parenteral (i.e., intramuscular, intraperitoneal and intravenous), rectal, and topical, oral administration and parenteral administration are particularly preferred.

The preferred pharmaceutical compositions are therefore those in a form suitable for oral administration such as tablets and suspensions and those suitable for parenteral administration such as solutions and emulsions.

The preferred daily dosage for oral administration is 0.5 to 100 mg/kg, preferably 5 to 50 mg/kg of body weight per day; in the case of intravenous administration 0.5 mg/kg to 20 mg/kg, preferably 1 mg/kg to 10 mg/kg, is preferred.

The coronary-vessel-dilating activity of compounds representative of those of the present invention is exemplified in Table 1 below:

Table 1

| Preparation example No. | Distinctly detectable rise in the oxygen saturation in the coronary sinus | |
|---|---|---|
| | Dose | Duration of action |
| 1 | 5 mg/kg i.v. | 30 mins |
| 5 | 10 mg/kg i.v. | 30 mins |

The coronary-vessel-dilating action was determined on narcotized heart-catheterized mongrel dogs by measuring the rise in oxygen saturation in the coronary sinus.

The following nonlimitative examples more particularly illustrate the present invention.

Example 1

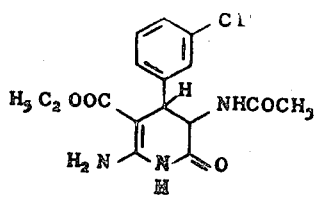

3-Acetylamino-6-amino-4-(3'-chlorophenyl)-3,4-dihydro-2-pyridone-5-carboxylic acid ethyl ester of melting point 270°C was obtained by boiling a solution of 22.2 g of 2-methyl-4-(3'-chlorobenzylidene)-1,3-oxazolinone-5 and 13 g of amidinoacetic acid ethyl ester in 200 ml of ethanol for 6 hours. Yield 61% of theory.

Example 2

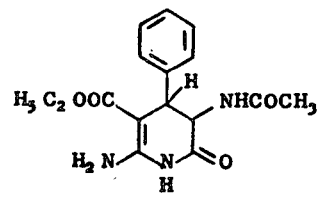

3-Acetylamino-6-amino-4-phenyl-3,4-dihydro-2-pyridone-5-carboxylic acid ethyl ester of melting point 228°C was obtained by boiling a solution of 17.1 g of 2-methyl-4-benzylidene-1,3-oxazolinone-5 and 13 g of amidinoacetic acid ethyl ester in 200 ml of ethanol for 6 hours. Yield 57% of theory.

Example 3

3-Benzoylamino-6-amino-4-(3'-nitrophenyl)-3,4-dihydropyridone-5-carboxylic acid ethyl ester of melting point 152°C was obtained by boiling a solution of 29.4 g of 2-phenyl-4-(3'-nitrobenzylidene)-1,3-oxazolinone-5 and 13 g of amidinoacetic acid ethyl ester in 350 ml of ethanol for 6 hours. Yield 53% of theory.

Example 4

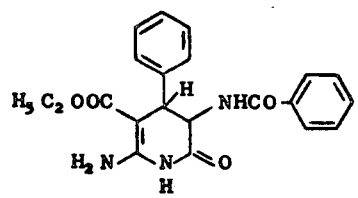

3-Benzoylamino-6-amino-4-phenyl-3,4-dihydro-2-pyridone-5-carboxylic acid ethyl ester of melting point 204° was obtained by boiling a solution of 24.9 g of 2-phenyl-4-benzylidene-1,3-oxazolinone-5 and 13 g of amidinoacetic acid ethyl ester in 350 ml of ethanol for 6 hours. Yield 61% of theory.

Example 5

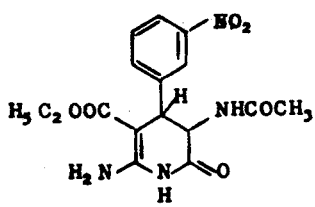

3-Acetylamino-6-amino-4-(3'-nitrophenyl)-3,4-dihydro-2-pyridone-5-carboxylic acid ethyl ester of melting point 258°C was obtained by boiling a solution of 23.2 g of 2-methyl-4-(3'-nitrobenzylidene)-1,3-oxazolinone-5 and 13 g of amidinoacetic acid ethyl ester in 250 ml of ethanol for 6 hours. Yield 45% of theory.

What is claimed is:

1. A 3,6-diamino-3,4-dihydro-2-pyridone of the formula

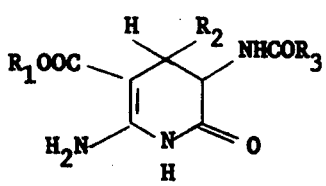

wherein $R_1$ is straight or branched chain alkyl of 1 to 6 carbon atoms; straight or branched chain alkenyl of 2 to 6 carbon atoms; straight or branched chain alkoxyalkyl of 2 to 6 carbon atoms;

$R_2$ is straight or branched chain alkyl of 1 to 6 carbon atoms; cycloalkyl of 3 to 6 carbon atoms; phenyl unsubstituted or substituted by 1 or 2 of the same or different substituents selected from the group consisting of alkyl of 1 to 4 carbon atoms, alkoxy of 1 to 4 carbon atoms, halo, nitro, cyano, trifluoromethyl, carb(lower alkoxy) of 1 to 4 carbon atoms in the alkoxy portion and $SO_n$-(lower alkyl) in which alkyl contains 1 to 4 carbon atoms and $n$ is 0 or 2; naphthyl; and $R_3$ is straight or branched chain alkyl of 1 to 6 carbon atoms; or phenyl unsubstituted or substituted by methyl, ethyl, methoxy, ethoxy, nitro, trifluoromethyl or chloro or bromo.

2. A compound according to claim 1 wherein $R_2$ is phenyl substituted by 1 substituent selected from the group consisting of methyl, methoxy, chloro, nitro, cyano, trifluoromethyl, and methylsulfonyl.

3. A compound according to claim 2 wherein $R_3$ is methyl or ethyl; or phenyl unsubstituted or substituted by methyl, ethyl, methoxy, ethoxy, nitro, trifluoromethyl, fluoro, chloro or bromo.

4. A compound according to claim 1 wherein
$R_1$ is methyl or ethyl;
$R_2$ is phenyl unsubstituted or substituted by nitro or halo; and
$R_3$ is methyl, ethyl or phenyl.

5. A compound according to claim 1 wherein
$R_1$ is ethyl;
$R_2$ is phenyl; chlorophenyl; or nitrophenyl; and
$R_3$ is methyl or phenyl:

6. The compound according to claim 1 which is

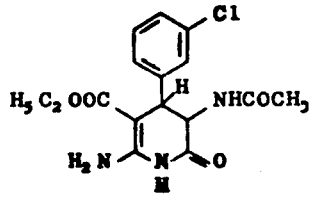

7. The compound according to claim 1 which is

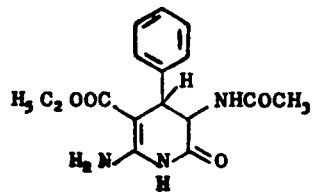

8. The compound according to claim 1 which is

9. The compound according to claim 1 which is

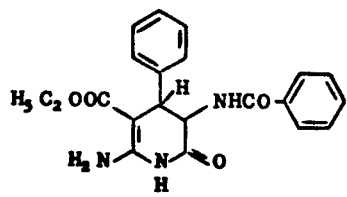

10. The compound according to claim 1 which is

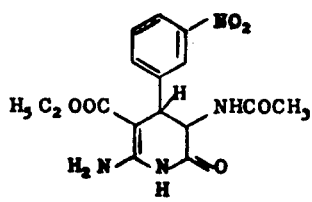

* * * * *